United States Patent [19]

Weiss et al.

[11] Patent Number: 4,698,301

[45] Date of Patent: Oct. 6, 1987

[54] ANGIOGENIC FACTOR PRODUCTION

[76] Inventors: Jacqueline B. Weiss, 69 Attwood Road, Didsbury, Manchester M20 OTB; Christopher R. Hill, 10 A Holmes Crescent, Wokingham, Berkshire, both of England

[21] Appl. No.: 556,174

[22] Filed: Nov. 29, 1983

[30] Foreign Application Priority Data

Nov. 30, 1982 [GB] United Kingdom ................. 8234066

[51] Int. Cl.$^4$ ...................... A61K 35/12; C12P 1/00; C08B 37/10
[52] U.S. Cl. ...................................... 435/41; 424/95; 435/240; 435/241; 536/21; 514/56
[58] Field of Search .................. 435/68, 70, 240, 241, 435/948, 41; 260/112 R; 424/95; 536/21; 514/56

[56] References Cited

U.S. PATENT DOCUMENTS

| 4,268,629 | 5/1981 | Tolbert et al. | 435/41 |
| 4,273,871 | 6/1981 | Tolbert et al. | 435/41 |
| 4,335,215 | 6/1982 | Tolbert et al. | 435/41 |

OTHER PUBLICATIONS

Weiss et al., Br. J. Cancer 1979, vol. 40, pp. 493–496, "An Angiogenic Factor Isolated from Tumours: A Potent Low-Molecular Weight Compound".
Watt, Sandra Louise, Diss. Abst. vol. 42(9), Mar. 1982, No. 3673B "Purification and Partial Characterization . . . Walker 256 Rat Carcinoma.
Merck Index 9th Edition, 1978, p. 103.
Schur et al. Biol. Abst., vol. 71(1), No. 4280, 1980, "Stimulation by a Low—Molecular Weight Angiogenic Factor . . . ".
Brown et al, Biol. Abst., vol. 70(3), No. 17559, 1980, "Angiogenic Factor from Synovial Fluid Resembling that from Tumors".
Fenselau et al., J. Biol. Chem. vol. 256, No. 18, Sep. 1981, pp. 9605-9611, "Tumor Angiogenic Factor".
R. A. Brown, et al, The Lancet, "Angiogenic Factor from Synovial Fluid Resembling that from Tumors", pp. 682-685, Mar. 29, 1980.
Chemical Abstracts, vol. 92, p. 469, "An Angiogenic Factor Isolated from Tumors: A Potent Low-Molecular-Weight Compound", Weiss, et al, 1980.
S. R. Ayad, et al, "DNA Uptake by a Mutant Streain of Lymphoma Cells", Nature, vol. 220, No. 5162, pp. 35-38, Oct. 5, 1968.
A. White, et al, "Changes in Camp and Fibronectin Concentrations in Adherent and Suspension Forms of a Hybrid Cell Line", Exp Cell Res 129, (1980), pp. 303-312.

Primary Examiner—Thomas G. Wiseman
Assistant Examiner—Robin Lyn Teskin
Attorney, Agent, or Firm—Cushman, Darby & Cushman

[57] ABSTRACT

New angiogenic factors of low molecular weight (under 1000), useful as treatment agents for wound healing and for biological assaying, made from in vitro cultures of a wide variety of tumor cells by a treatment which breaks up the proteinaceous tumor angiogenesis factors ("TAF") in them and liberates the more mobile low molecular weight factors. The treatment can be applied to cell extracts or the aqueous portion of the culture, and the proteinaceous part may be rendered insoluble or captured chemically so as to release the new factor. Separation techniques which can be used include solvent extraction of dried liquid fractions, using polar solvents such as ethanol, and the liberated factor can be purified chromatographically using adsorbents for which the factor has affinity, especially a basic adsorbent and preferably polysaccharide-based, followed by elution.

9 Claims, No Drawings

ANGIOGENIC FACTOR PRODUCTION

This invention relates to new angiogenic factors and methods for their production and purification.

An angiogenic factor is a material which has the property of being able to initiate endothelial cell mitosis and direct the newly-formed endothelial cells to form new capillaries orientated towards the source of the factor (the process known as angiogenesis).

Angiogenesis is a process which is closely associated with the action of collagenolytic enzymes (for example collagenase). The connection is not entirely clear, but it appears to be based upon the action of a humoral factor (an angiogenic factor) which first diffuses through connective tissue and there activates a pro-collagenase which initiates a degradative process which acts upon the matrix between individual cells. This action forms channels in the tissue, along which endothelial cells can congregate to form new capillaries.

Angiogenic factors have potential value for biological testing and assay purposes in tissues and plasma using a radio-immune assay technique, in which the angiogenic factor is the antigen, and also as treatment agents for wound healing, for example in humans.

It is known to produce a variety of proteinaceous angiogenic factors (often of unknown identity) from cells, and from tumor cells in particular. For example it is known to produce angiogenic factors from cells grown in vitro in a nutrient culture medium using various cell lines (see for example Tolbert et al., U.S. Pat. Nos. 4,209,587, 4,210,718, 4,210,719, 4,217,412, 4,225,670, 4,229,531 and 4,229,532). These are referred to as tumour angiogenesis factors ("TAF"). They are high molecular weight materials (for example Tolbert quotes molecular weights in the range 35,000 to 300,000) and in consequence are not mobile enough to diffuse in tissues as well as is usually desired and can tend to be antigenic in the host.

It is also known to produce angiogenesis factors of lower molecular weight from whole tissues or body fluids, but these have the very great disadvantage that their preparation from whole tissues or body fluids has required tumors to be grown in animal hosts, that isolation by use of an antibody affinity method which cannot readily be reproduced, and that very little active factor can be recovered from either tumor extracts or body fluids.

We have now discovered that these disadvantages can be overcome, and angiogenic factors of low molecular weight can be made readily from the culture of tumor cells in vitro by a procedure in which the factor is extracted from the culture medium using a modified extraction technique in which the proteinaceous material (which appears to act as a carrier for the low molecular weight angiogenic factor) is made to release the low molecular weight angiogenic factor and is separated from it.

Thus, according to the present invention we provide an improved method for the preparation of angiogenic factors having low molecular weight, which comprises growing tumor cells in a nutrient culture medium in vitro, characterised in that the resulting culture is treated to separate proteinaceous materials from it before proceeding to isolate the angiogenic factor from it.

The resulting angiogenic factors are believed to be new but are of unknown chemical constitution. They have anionic characteristics and undoubtedly are of low molecular weight, as is demonstrated by standard techniques for measurement. In particular, they are found to have molecular weights (alternatively termed "molecular masses") below 1000, and especially in the range of 300 to 600, as determined by a gel filtration method using markers of known molecular weight. They also appear to have some degree of oleophilic character.

The tumor cells for use in the method of the present invention may be any tumour cells, but are preferably those described in "non-attaching" because these are better for the purposes of carrying out culture in liquid suspension and grow well in vitro in a suspension culture medium. They may be any of the known animal or human tumor cells, for example lung tumor, melanoma, lymphoma or lymphoblastic cells, more specific examples of which include cell lines from a mouse lymphoma, a human lymphoblastic leukemia and a human Birkitt's lymphoma. Some tumor cells will be more efficient or convenient in use than others, but the optimum for use in any particular circumstances (for example to suit the culture medium or culture methods used) can be determined by simple trial. A very convenient example is the lymphoma cell line P.388 (which was originally isolated in 1964) and P.388-F36 (which was cloned from it in 1974).

The culture medium may be any which is appropriate to sustain growth of the cells concerned. An especially convenient medium is Dulbecco's modification of Eagle's minimum essential medium (MEM). Other media may be used if desired, for example any of the suspension culture media known in the art. These conventional culture media contain known essential amino acids, mineral salts, vitamins and carbohydrates. The media may optionally be fortified by addition of supplements, for example further amounts of carbohydrates (for example glucose) and/or mammalian sera, for example fetal bovine serum.

Growth of the tumor cells in the culture medium is preferably carried out in agitated liquid suspension.

Suitable equipment and procedures for growing the cultures of the cells may be any of those available to the expert in the art, and may be varied considerably at the desire of the operator. Typical general conditions will depend to some extent upon the particular cell line used, but examples are:

(a) culture temperatures up to approximately 38 degrees Celsius, as above this temperature the cells usually tend to suffer damage and not to undergo sustained growth. Our preference is for temperatures in the range 35 to 38 degrees Celsius, and especially for approximately 37 degrees Celsius.

(b) culture times of up to 8 days, but preferably in the range 2 to 4 days. Growth over longer periods can be used if desired, though the rate of growth may then fall to an uneconomic level insufficient to justify the extra time.

The first stage is recovering the low molecular weight factor from the cell culture is to prepare an aqueous extract.

This aqueous extract may be prepared in a variety of ways, of which the first and most convenient is usually a treatment of the cell culture to separate from it the cells and any other insoluble matter present. This is very conveniently done by centrifuging; if desired other conventional physical methods means may be used, but in general we find that centrifuging is the most simple, convenient and speedy.

The time and intensity of the centrifuging can vary, and the usual indication of the requirements is that substantially all the cells should be sedimented in a conveniently speedy manner, consistent with the economics of the particular centrifuging system used. After the achievement of adequate sedimentation by centrifuging, the sedimented cells are removed in conventional manner, for example by decantation or drawing off the supernatant liquid from above the sedimented cells.

The aqueous extract may also be made from the cells by washing them with fresh culture medium or buffer. To achieve this, the separated cells obtained from the initial separation stage (for example centrifuging) may be mixed with an aqueous extraction medium (buffer, culture medium or water), agitated thoroughly, and then subjected to the separation procedure (for example centrifuging) again, so as to obtain an aqueous extract and a reject fraction comprising the cells. This procedure may be repeated as often as desired, though it may be uneconomic to carry it out more than twice.

The aqueous extract may also be made from the cells themselves by breaking them up to recover the angiogenic factor present in them. This may be done using standard procedures, for example by homogenisation, by extraction with water, by freezing and thawing, or by combinations of such techniques. The cell debris and insoluble matter can be removed from the resulting liquid using similar techniques to those used for separating the cells from the culture mixtures, for example by centrifuging, dialysis, diafiltration, or combinations thereof.

The aqueous extract which is used for recovery of the angiogenic factor may comprise any of the forms of extract described above or any combination of these. Thus, it may comprise either the initially separated fraction of the cell culture or an aqueous extract from the separated cells, but preferably comprises both combined together, as active factor is present in both. There is usually more of the desired factor in the culture liquor than in the cell extract, but the choice of exactly which liquids to use and which to discard is often a matter of economic consideration and the amount recovered needing to justify the cost of the handling procedures.

As a precaution, a cell homogenate or extract should at first be treated separately so as to minimise the risk of any inhibitors in the cells rendering the factor less stable or more difficult to isolate. Whether this proves to be a problem in practice, so that separate treatment is needed, can easily be determined by simple trial.

The aqueous extract may be concentrated to reduce its bulk before being treated to remove proteinaceous materials. This is usually convenient, but is not always essential.

One method of concentration comprises evaporating the aqueous extract. An alternative method comprises dialysis against water (usually purified or distilled water) to remove soluble electrolytes and the like. In this the factor is retained in the retentate, apparently associated with various proteinaceous materials; most of the low molecular weight factor does not migrate to the water side of the dialysis membrane, though small proportions may do so and such minor losses are usually considered to be economically acceptable.

Another alternative method is diafiltration, in which the functions and considerations are very similar to those for dialysis. The factor at this stage is mainly retained in the retentate, and little or none is lost in the diafiltrate.

According to one procedure, the aqueous extract is evaporated to dryness and then the resulting dried residue is agitated and intimately mixed with a solvent which dissolves the factor but leaves the bulk of the proteinaceous material as an insoluble residue which can be removed and discarded. Such solvents include polar solvents, and especially a lower alkanol having up to 8 carbon atoms in the molecule, but the preferred solvent is methanol, ethanol, or mixtures thereof.

An alternative method comprises insolubilising the proteinaceous material so as to precipitate it from the solution and enable it to be removed.

Other ways may be evident to the expert in the art.

When using the evaporation technique, this may be carried out by any convenient conventional means. Care should be taken to ensure in particular that the extract does not suffer degradation to any appreciable extent, for example by exposure to temperatures high enough to degrade the factor. It is therefore preferred to use a drying technique which can do this satisfactorily, and examples are evaporation under reduced pressure and freeze-drying, and combinations of these, as they virtually eliminate risk of thermal degradation.

When evaporating to dryness, as a preliminary to a solvent extraction step, the extent of the drying required depends upon such factors as the solvent which is to used for extracting the factor. In general it is preferable that drying should be carried on to a stage at which substantially all the water has been removed. Absolute dryness is not essential, but it is preferred that the drying should be at least to the stage at which a free liquid phase is no longer present, and preferably to the stage at which the dried residue contains only little water, as this minimises the effect of residual water on the solvent power of the solvent used and also the risk of any water remaining undissolved in the solvent during the solvent extraction stage and forming a separate phase which could interfere with handling of the mixture.

This dried residue may contain one or more of the proteinaceous angiogenic factors ("TAF") such as those of Tolbert et al., and for the purposes of this invention such a material may be separated specifically if desired, and then treated to remove the proteinaceous portion, but this is usually not an economically attractive variant.

The dried residue is then extracted with a solvent (preferably an organic solvent) which dissociates the factor from the proteinaceous materials and dissolves the bulk of the factor but not the proteinaceous materials. Such a solvent may be in particular a polar organic solvent, for example a lower aliphatic alcohol containing up to 8 carbon atoms in the molecular, which may be of straight or branched chain structure. The preferred alcohols for this purpose are methanol or ethanol (or mixtures thereof, for example mixtures with water) but others may be used if so desired, for example propanol, isopropanol, and mixtures thereof.

The extraction may be carried out in any convenient form of conventional apparatus, for example by batchwise or continuous extraction techniques. For best results, the solid should be agitated with the solvent for a time which is sufficient to promote thorough contact and extraction. Extraction can also be assisted by having the solid in as finely divided state as is practicable, for example in a finely divided state, for example in a pulverised or powdered state.

An alternative procedure comprises precipitating the proteinaceous materials from the aqueous extract by addition of suitable precipitants. Examples of suitable materials for this purpose include acids and water-miscible polar solvents, for example the lower aliphatic alcohols and especially methanol and/or ethanol. Combinations of precipitants can be used if desired. Optionally, the bulk of liquid may be minimised by a prior concentration of the aqueous extract, for example by partial evaporation (conveniently by partial freeze-drying, for example to about one-fifth of the original bulk), but this is not essential.

The separation of the proteinaceous material and the low molecular weight angiogenic factor can also be brought about by the addition of any material which competes for the proteinaceous material and thereby releases the low molecular weight angiogenic factor from combination with the proteinaceous material. This release enables the low molecular weight angiogenic factor to behave in solution as an unbound low molecular weight material, with the result that it becomes recoverable by methods which can separate low molecular weight materials from high molecular weight materials (for example proteins) for example by dialysis or diafiltration, when it then can be obtained in the dialysate or diafiltrate. Examples of materials which can compete for the proteinaceous material in this way include proteoglycans, but we prefer to use a glycosaminoglycan, for example hyaluronic acid, or even glucuronic acid. Other examples include sulphated glucuronic acid, but there may be used any anionic material which retains its anionic character sufficiently to achieve this desired competitive action, especially at pH values of the order of 7 to 9, at which the factor is most stable. The action of the additive can be enhanced by the presence of soluble salts, especially polyvalent metal salts, for example magnesium chloride.

Solutions of the angiogenic factor thus obtained may be purified to remove unwanted components and to recover the factor. This may be applied to a solution obtained by either route described above. It is preferred that when the route used gives a solution containing appreciable proportions of organic solvent, the organic solvent be removed as much as is practicable. Complete removal is not essential, but is preferred because the presence of organic solvents may interfere to some extent with subsequent steps. One procedure which is useful, especially when the factor has been recovered by solvent extraction of the product obtained by evaporating the aqueous extract to dryness, is to remove substantially all the organic solvent by evaporation and then to redissolve the residue in water to form an aqueous solution.

The further treatment of the resulting solution resulting from the removal of proteinaceous material can be carried out in a variety of ways which utilise the anionic and other properties of the low molecular weight factor.

This may be done advantageously by chromatography, preferably by using an adsorbent which binds the new angiogenic factor and takes it out of the solution and leaving unwanted components in the solution, which is then rejected. The adsorbent carrying the adsorbed factor can then be washed in conventional manner, using a wash liquid which does not elute appreciable amounts of the factor, and then the adsorbed angiogenic factor can be displaced or desorbed from the adsorbent by treatment with a reagent solution which enables it to be eluted.

A suitable adsorbent is a basic adsorbent, as this utilises the fact that the factor has anionic properties. Such adsorbents may be organic or inorganic in nature, for example a siliceous material appropriately treated or coated to give it basic properties, but very conveniently may be a solid material having a polysaccharide matrix. The surface of the adsorbent (whatever the nature of its matrix) should be a basic one, achieved for example by appropriate chemical treatment to impart basic character, as is well known in the chromatographic art.

Examples of suitable adsorbents include cellulose-derived materials having basic character. A particular example of such a material is diethylaminoethyl-cellulose, which is referred to for convenience as "DEAE Cellulose" and is available commercially from Whatman Biochemicals.

The adsorption procedure may be carried out by dissolving the impure factor (for example that obtained by the above-described alcohol extraction) in a mildly alkaline aqueous solution and passing this alkaline solution over the adsorbent. The alkaline solution is preferably of a pH in the range 7 to 9. A very convenient alkaline solution for this purpose is an aqueous solution of ammonium bicarbonate, a 50 millimolar aqueous solution of which has a pH of approximately 7.9. If an aqueous solution is directly available, for example after precipitation of proteinaceous material, this should be rendered slightly alkaline in similar manner. When the solution has passed through the adsorbent and the factor has been taken up from the solution, unwanted materials which are not bound to the adsorbent, can be washed away by further quantities of the same alkaline solution or buffer.

A suitable reagent for displacing the adsorbed angiogenic factor from the adsorbent is an aqueous solution of an ionic inorganic salt of high ionic strength, for example sodium chloride. This is preferably buffered to a pH in the range 7 to 9. In the case of elution of the factor from a DEAE cellulose adsorbent, a very suitable solution for eluting the factor is an aqueous solution of sodium chloride at an ionic strength in the range 0.2 to 0.3 molar; solutions below this concentration range do not elute the factor appreciably, and so may be used to elute other adsorbed materials preferentially.

Elution can be achieved by use of any salt solution, (for example a sodium chloride solution) above about 0.15 molar, and preferably above 0.2 molar.

The apparatus and techniques for this chromatographic adsorption and elution may be any of those known in the art.

An alternative method for purifying the angiogenic factor comprises adsorbing the factor from aqueous solution by contact with an adsorbent having a fatty surface. The adsorbent may be made mainly from a material having the desired fatty characteristics or, more conveniently, from a substrate material or carrier having a surface coating of a material of the desired fatty properties. As such substrate materials there may be use any of a wide variety, for example silica, alumina, silico-aluminates, or mixtures thereof, made and/or graded to appropriate particle size. The coating material may be of any chemical structure which enables it to be held to the surface of the substrate, and may for example be a fatty acid or a fatty alcohol. Preferred fatty compounds for the purpose are those having in their structure an aliphatic chain of at least 10 carbon atoms. Most conveniently, compounds of C16 or C18 structure are used, for example stearic acid, stearyl alcohol, and the like.

The angiogenic factor can then be displaced from the adsorbent by elution with a solvent less polar than water. This may conveniently be defined as a solvent with eluting power (polarity in the range 0.3 to 1.0) with respect to silica according to the definitions given by L. R. Snyder ("Principles of Absorption Chromatography," published by M. Dekker, New York 1967. Such solvents include for example a lower aliphatic alcohol (especially methanol and/or ethanol).

Such a solvent, for example an alcohol, may be used as such or may be diluted with a limited amount of water. When silica coated with a surface layer of stearic acid is used as adsorbent, a very convenient elution solvent is aqueous methanol containing a proportion of methanol and/or ethanol in the range 40% to 80% by volume.

An alternative adsorbent material is collagen, as the angiogenic factor binds strongly to collagen. This can be used for example in the form of a Type I collagen-affinity column; this contains collagen supported upon a support comprising a polysaccharide or other support activated e.g. by cyanogen bromide. The adsorbed factor can be removed again from the collagen adsorbent and recovered by elution with a solution of a mildly acidic salt for example ammonium acetate at a pH of approximately 3.5.

The product of our invention is a low molecular weight angiogenic factor which is freely dialysable and has the ability to activate fully fibroblast pro-collagenase and other latent collagenolytic enzymes.

As the factors are so highly active, even in amounts which cannot be detected by chemical means, it is not usually practicable or necessary to try to obtain them as dry solids, though they can if desired be obtained in this form by appropriately drying solutions of them at temperatures which do not bring about their decomposition.

More conveniently, however, they may be made, kept or stored, and used as solutions, most conveniently in water (with or without buffers to maintain a pH at which they are stable.

Alternatively, they may be converted to "bulked solids" (i.e. deposited on a suitable solid carrier) to increase their volume and make them easier to handle and measure out for use. Suitable carriers for this purpose may be any materials which serve as pharmaceutically acceptable carriers, i.e. which are suitably inert and preferably can be dissolved in water or other media in which the factors may be used. Examples of such carriers include carbohydrates (for example lactose), proteins (for example bovine serum albumen), and salts (for example sodium chloride), and mixtures thereof.

The activity of the factor in stimulating the action of pro-collagenase is enhanced by the presence of heparin. This synergistic action provides a basis for increasing the usefulness of the angiogenesis factor of the present invention, and as a basis for new and useful compositions comprising a new angiogenic factor made as described above and herparin as a potentiating additive.

For use, the factor may be applied in a manner which is conventional for materials of their biological activity and utility. Thus for example, they may be mixed with pharmaceutically acceptable carriers, diluents, adjuvants and the like as may be appropriate, for example in the formulation and preparation of wound-treatment dressings, compositions and the like.

The invention is illustrated but not limited by the following Examples, in which the parts and percentages are by weight unless otherwise stated.

EXAMPLE 1

(STEP 1)

Tumor cells of the type P388-F36 are grown to a high cell density (approximately 2 to $3 \times 10^6$ cells per ml) in 1 liter of Delbecco's modification of Eagle's MEM nutrient culture medium to which has been added 15% of fetal calf serum, contained in spinner culture flasks at 37 degrees Celsius for 4 days. The culture is then cooled to ambient temperature.

(STEP 2)

The resulting culture (conveniently in batches of about 200 ml) is then centrifuged for 5 minutes at 500 G. in a refrigerated centrifuge at approximately 5 degrees Celsius to sediment the cells, and then the supernatant liquid is separated from the sedimented cells by decantation or drawing off through a suction line.

This supernatant liquid is dialysed against distilled water (3 times with 10 volumes) to remove dissolved salts, and then the retentate is freeze dried.

As an alternative treatment in this stage, the liquid may be diafiltered instead of dialysed.

(STEP 3)

The resulting dried residue is then thoroughly agitated with 200 ml of absolute ethanol (99–100%) for 2 to about 4 hours at 4 degrees Celsius to extract the angiogenic factor into solution, and then the mixture is centrifuged to sediment out the solids (cells and other insolubles).

The resulting supernatant ethanolic solution is then separated from the sediment by decantation or drawn off through a suction line, and then the residual pellet of sedimented cells is re-extracted by thorough agitation with a further amount of alcohol in similar manner and centrifuged again. The two ethanolic extracts are then combined and evaporated to dryness under reduced pressure, taking care that the temperature does not rise above 37 degrees Celsius.

(STEP 4)

The solid resulting from this extraction with ethanol is dissolved in 10 to 20 ml of an aqueous buffer solution of 50 millimolar ammonium bicarbonate (pH 7.9) at 4 degrees Celsius, and this solution is passed through a chromatographic column (10 cm. high and 1 cm. diameter) packed with diethylaminoethyl cellulose which has been equilibrated at the same temperature with the same buffer. The column is then washed with more of the buffer solution to remove any unbound materials until the emergent liquid contains no detectable organic components. This is conveniently determined by passing the emergent liquid through a detection cell in an adsorbing monitor using a 206 nanometer filter.

Bound material on the column is then eluted by passing sodium chloride solution down the column at a progressively increasing concentration (convex salt gradient) rising from zero to 0.3 molar, prepared in a constant level mixing device from (a) 65 ml of the ammonium bicarbonate buffer solution and (b) 100 ml of the same buffer containing 1.0 molar sodium chloride. The column is then finally washed with the buffer solution containing 1.0 molar sodium chloride.

The fraction eluted when the elution profile was in the range 0.2 to 0.3 molar with respect to the sodium chloride was collected separately from the rest. This fraction was found by experimental testing for angiogenic activity by the chick chorioallantoic membrane ("CAM") bioassay system to contain most of the angiogenic activity from the original ethanol extract.

(STEP 5)

The active fraction from Stage 4 was de-salted by gel filtration on a column (44 cm high by 4.4 cm diameter) of Bio-Gel P2 in 10% (v/v) propanol-2, the elution being performed at 4 degrees Celsius with an ascending flow rate of 45 ml per hour.

The active factor thus obtained was found to have the following properties:

1. It stimulates neo-vascularization in the chick chorioallantoic membrane assay (i.e. is CAM-active).

2. At nanomolar concentrations it is able to activate skin fibroblast pro-collagenase to a greater extent than can be achieved with the commonly used chemical activator "Mersalyl" and to approximately the same extent as mat be achieved by trypsin.

3. Both activities 1 and 2 above can be enhanced with heparin.

4. It is able to stimulate mitosis in capillary endothelial cells grown on a collagen substratum.

5. It is of low molecular weight as demonstrated by both dialysis and gel filtration techniques.

6. It is anionic as demonstrated by its binding to DEAE cellulose.

7. It binds to $C_{18}$-coated silica when applied from aqueous solution. (This may be attributable to the fatty part or to the silica.)

8. It binds strongly to collagen.

EXAMPLE 2

The activity detected experimentally is illustrated in the following Table, in which the activity of the angiogenesis factor made in the manner described in Example 1 (designated as "ESAF"=Endothelial Cell-Stimulating Angiogenesis Factor), alone and in conjunction with heparin, is compared with "Mersalyl", EDTA (Ethylenediamine-tetracetic acid, which inhibits collagenase activity) and heparin as stimulants of the enzyme, pure skin fibroblast pro-collagenase.

"Mersalyl" is a synthetic organic mercurial compound which is routinely used to activate latent collagenolytic enzymes, and is obtainable from Evans Medical, Liverpool, U.K.

The factor alone had no effect against active skin collagenase.

In Experiment 2 the factor is used at a higher dilution than in Experiment 1.

|  | Experiment 1 | Experiment 2 |
|---|---|---|
| Enzyme alone | 115 cpm | 10 cpm |
| Enzyme + Mersalyl | 2957 | 2932 |
| Enzyme + EDTA | 115 | 11 |
| Enzyme + Heparin | 154 | 48 |
| Enzyme + ESAF | 6377 | 530 |
| Enzyme + ESAF and Heparin | 6812 | 1334 |

In these measurements quoted, "cpm" means the number of counts per minute in the radioactive assay using the materials and procedures detailed below.

The materials and procedures used were as follows:

The Enzyme:

Human skin fibroblast pro-collagenase was prepared from serum-free human skin fibroblast conditioned medium by a modification of the method of Stricklin et al., (1978, Biochemistry, Vol. 17, pages 2331-2337).

The serum-free medium was applied to a Sephacryl S.200 column (80×2.5 cm) and eluted with Tris-HCl buffer at pH 7.6 containing 0.2 molar sodium chloride and 0.01 molar calcium chloride. The pro-collagenase peak fractions of highest concentration were bulked and used without concentrating.

The Substrate:

Types I and III collagens were prepared from bovine fetal calf serum by the method of Epstein (1974, J. Biol. Chem, Vol. 249, pages 3225-3231) The collagens were labelled with tritium using the method of Gisslow and McBride (1975, Analytical Biochemistry, Vol. 68, pages 70-78)

Complete hydrolysis of 50 micrograms each of Type I and Type III collagen catalysed by bacterial collagenase from *Clostridium Hystolycum* (from Sigma, London) yielded 12200 and 12000 counts per minute respectively.

The Assay:

Type I or III collagen (50 micrograms) was dissolved in 0.05 molar Tris buffer containing 0.2 molar sodium chloride and 0.01 molar calcium chloride (25 microliters) and pre-incubated for 30 minutes at 36.5 degrees. The same buffer (200 microliters) containing either "Mersalyl" (25 millimolar), angiogenesis factor, or EDTA (25 millimolar), Mersalyl plus EDTA, angiogenesis factor plus EDTA, or bacterial collagenase was added together with 200 microliters of buffer containing pro-collagenase, the total volume adjusted to 500 microliters with buffer and the mixture was incubated at 36.5 degrees for 16 hours. Following incubation 250 microliters of Tris buffer containing 6 molar sodium chloride was added to each buffer to precipitate unreacted collagen. Tubes were incubated at 36.5 degrees for 30 minutes more and then centrifuged at 1720 G for 30 minutes at 25 degrees Celsius.

Aliquots (200 microliters) of supernatant were counted in 5 ml of a scintillant [a mixture of (a) toluene containing 5% w/v of 2,5'-diphenyl oxazol ("PPO") and 0.1% w/v of 1,4'-bis-(5-phenyl-2-oxazol) benzene ("POPOP") and (b) "Triton" X.100 in the proportion 6 to 3 by volume], the whole mixture containing 1% perchloric acid. Each test was carried out in duplicate and each sample was counted in duplicate. ("Triton" X.100 is a commercially available surfactant.)

The appropriate controls, i.e. all reactants and components with the pro-collagenase substituted by 200 microliters of Tris buffer, were carried out for each assay and the counts per minute were subtracted from the test results.

We claim:

1. A method for the preparation of an angiogenic factor of molecular weight of between 300 and 600, and having the ability to activate pro-collagenase, which comprises the steps of:
   (1) growing tumour cells in vitro in an aqueous nutrient culture medium by a suspension culture procedure so that said factor is released into the culture medium,
   (2) separating the grown cells from the culture medium to obtain an extract containing said angiogenic factor in admixture with proteinaceous materials,
   (3) treating the extract from step (2) to remove proteinaceous materials from it, and (4) recovering the angiogenic factor of molecular weight of between 300 and 600 from the extract remaining from step (3).

2. A method as claimed in claim 1 wherein the separated culture medium from step (2) is evaporated to dryness and the dried residue is extracted with a sufficient amount of a solvent which dissolves the low molecular weight angiogenic factor but not the proteinaceous material.

3. A method as claimed in claim 1 wherein the separated culture medium from step (2) is treated to render the proteinaceous material insoluble, and the insolubilised proteinaceous material is separated to leave an aqueous solution containing the low molecular weight angiogenic factor.

4. A method as claimed in claim 1 wherein the separated culture medium from step (2) is treated with a material which competes with the low molecular weight angiogenic factor for the proteinaceous materials and thereby releases the low molecular weight angiogenic factor from combination with the proteinaceous material, and then separating an aqueous fraction containing the low molecular weight angiogenic factor by dialysis and/or diafiltration.

5. A method as claimed in claim 1 wherein the low molecular weight angiogenic factor recovered by separation from the proteinaceous material is purified by adsorption on a basic adsorbent, and then eluted therefrom.

6. A method as claimed in claim 1 wherein the low molecular weight angiogenic factor recovered by separation from the proteinaceous material is purified by adsorption on an adsorbent comprising a fatty material on an inorganic substrate, and then eluted therefrom.

7. A method as claimed in claim 1 wherein the low molecular weight angiogenic factor recovered by separation from the proteinaceous material is purified by adsorption on an adsorbent comprising a collagen and then eluted therefrom.

8. A low molecular weight angiogenic factor which is anionic and water soluble, has the ability to activate procollagenase, has a molecular weight of between 300 and 600, binds to $C_{18}$-coated silica, is CAM-active, and stimulates mitosis in capillary endothelial cells, obtained by a process as claimed in claim 1.

9. A composition comprising a low molecular weight angiogenic factor as claimed in claim 8 in combination with heparin.

* * * * *